United States Patent [19]

Mayerhoefer et al.

[11] 4,035,448

[45] July 12, 1977

[54] ORGANIC COMPOUNDS

[75] Inventors: Horst Mayerhoefer, Oberwil; Wolfgang Mueller, Neuallschwil; Urs Sollberger, Fullinsdorf; Rainer Wolf, Allschwil, all of Switzerland

[73] Assignee: Sandoz Ltd., Basel, Switzerland

[21] Appl. No.: 565,708

[22] Filed: Apr. 7, 1975

Related U.S. Application Data

[62] Division of Ser. No. 364,629, May 29, 1973, Pat. No. 3,890,409.

[30] Foreign Application Priority Data

June 1, 1972 Switzerland .................... 8117/72
June 14, 1972 Switzerland .................... 8898/72

[51] Int. Cl.$^2$ .................... C07F 9/15; C08K 5/52
[52] U.S. Cl. .................... 260/937; 260/45.8 R
[58] Field of Search .................... 260/937, 45.8 R

[56] References Cited

U.S. PATENT DOCUMENTS

| | | | |
|---|---|---|---|
| 2,834,798 | 5/1958 | Hechenbleikner et al. | 260/937 X |
| 2,839,563 | 6/1958 | Hechenbleikner | 260/937 X |
| 2,883,411 | 4/1959 | Lanbam | 260/937 |
| 3,006,946 | 10/1961 | Lanham | 260/937 X |
| 3,149,181 | 9/1964 | Warren | 260/45.8 R |
| 3,415,906 | 12/1968 | Shepard et al. | 260/45.8 R X |
| 3,467,733 | 9/1969 | Dever et al. | 260/937 X |
| 3,509,091 | 4/1970 | Cleveland et al. | 260/45.8 R |

Primary Examiner—Sandra M. Person
Attorney, Agent, or Firm—Gerald D. Sharkin; Richard E. Vila; Thomas C. Doyle

[57] ABSTRACT

The present invention relates to phosphorus containing compounds and more specifically to phosphorous and phosphoric acid esters of the formula,

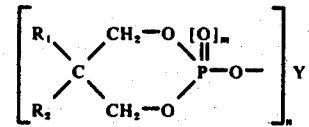

wherein
$R_1$ and $R_2$ are each hydrogen or alkyl,
$n$ is an integer 1 or 2, and
Y is a mono or divalent aromatic radical.

The compounds are useful as flame retardants for, e.g., plastics materials.

8 Claims, No Drawings

ORGANIC COMPOUNDS

This is a division of application Ser. No. 364,629 filed May 29, 1973, now U.S. Pat. No. 3,890,409.

The present invention relates to phosphorus containing compounds and more specifically to phosphorous and phosphoric acid esters.

The present invention provides compounds of formula I,

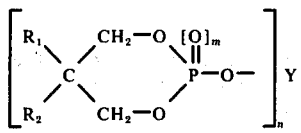

wherein $R_1$ and $R_2$ are each, independently, hydrogen or alkyl of 1 to 5 carbon atoms,
and either $n$ is the integer 1
and Y is a radical $Y_1$,

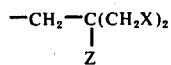

wherein each X is, independently, chlorine or bromine and Z is alkyl of 1 to 4 carbon atoms or —$CH_2X$ wherein X is as defined above, or a radical $Y_2$,

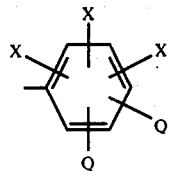

wherein each X is, independently, as defined above, and
each Q is, independently, hydrogen, methyl, chlorine or bromine,
or $n$ is the integer 2
and Y is a radical $Y_3$,

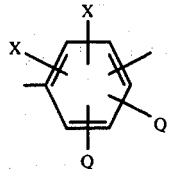

wherein each X and Q are, independently, as defined above,
or a radical $Y_4$,

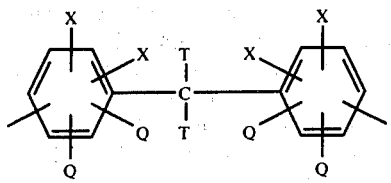

wherein each X and Q are, independently, as defined above, and each T is, independently, hydrogen or alkyl of 1 to 4 carbon atoms,
and $m$ is zero or the integer 1, with the proviso that when $m$ is zero, at least one X of $Y_2$ is bromine and at least one Q of $Y_3$ is chlorine or bromine.

When either or both of $R_1$ and $R_2$ are alkyl, this is preferably of 1 to 4 carbon atoms, particularly 1 to 3 carbon atoms, especially methyl or ethyl, particularly methyl.

When either or both of $R_1$ and $R_2$ are alkyl of 3 to 5 carbon atoms, this may be straight or branched chain.

Representative examples of alkyl significances of $R_1$ and $R_2$ are methyl, ethyl, n-propyl, n-butyl, n-pentyl, isopropyl, isobutyl, sec. butyl, tert. butyl and branched pentyl.

When one or each T is alkyl, this is preferably of 1 to 3 carbon atoms, particularly methyl or ethyl, especially methyl.

When one or each T is alkyl of 3 or 4 carbon atoms, this may be straight or branched chain.

Representative examples of alkyl significances of T are methyl, ethyl, n-propyl, isopropyl and tertiary butyl.

When Z is alkyl, this is preferably of 1 to 3 carbon atoms, e.g. methyl or ethyl. Preferably, however, Z is —$CH_2X$.

Examples of $Y_2$ are as follows:

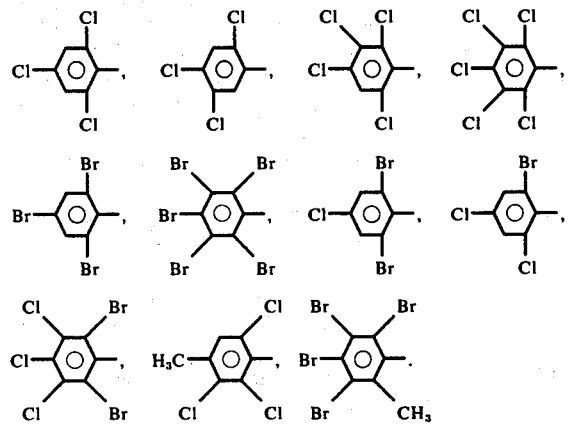

Preferred significances of Y contain at least one, and more preferably two, bromine atoms, especially when $m$ of formula I is zero.

The present invention also provides a process for the production of a compound of formula I, which comprises
a. condensing a compound of formula II,

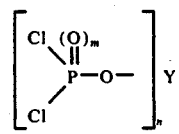

wherein $m$, $n$ and Y are as defined above, with a compound of formula III,

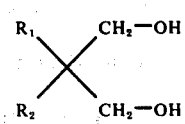

wherein $R_1$ and $R_2$ are as defined above, in a molar ratio of $1:n$, or, b. condensing a compound of formula IV,

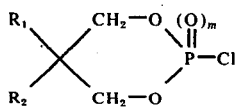  IV wherein $m$, $R_1$ and $R_2$ are as defined above, in a molar ratio of $n:1$ with a compound of formula V, $$Y+OH)_n \quad \quad V$$

wherein Y and $n$ are as defined above.

The process in accordance with variant a) may be effected as follows viz:

The compound of formula II is preferably dissolved in an inert solvent such as a hydrocarbon solvent, e.g. benzene, toluene, xylene or cymene, an ether solvent, e.g. diphenylether or tetrahydrofuran, or an halogenated hydrocarbon as solvent, e.g. trichloroethylene, and a compound of formula III added thereto. The reaction is preferably effected in the presence of an acid binding agent. Examples of suitable acid binding agents are heterocyclic aromatic amines such as pyridine, trialkylamines such as triethylamine and dialkylanilines such as dimethylaniline. The reaction is preferably effected under anhydrous conditions. Preferably, the addition of the compound of formula III to the compound of formula II is effected at room temperature, if necessary with external cooling to room temperature, and the compounds allowed to react for an initial period at this temperature, e.g. for a period of between ½ and 2 hours. After the initial reaction period, the temperature of the reaction mixture may be raised to above room temperature, e.g. between 40° and 70° C, preferably to about 50° C, and the reaction mixture maintained at this raised temperature for a prolonged period, e.g. between 5 and 50 hours, preferably between 5 and 40 hours.

After the reaction, the reaction product may be worked up in a conventional manner.

In one mode of effecting process variant a) of the invention, the compound of formula II is produced in situ, and the process is continued without isolation of the compound of formula II.

The process in accordance with variant b) may be effected as follows viz:

The compound of formula IV is preferably dissolved in an inert solvent such as a hydrocarbon solvent, e.g. benzene, toluene, xylene or cymene, an ether solvent, e.g. diphenylether or tetrahydrofuran, or a halogenated hydrocarbon, e.g. trichloroethylene, and a compound of formula V added thereto. The reaction is preferably effected in an inert atmosphere, e.g. a nitrogen atmosphere, and under anhydrous conditions. The reaction period may vary depending on the reactants and reaction conditions. However, a period of between 10 and 20 hours, e.g. 15 hours, is generally suitable. The reaction mixture may be heated, conveniently to the reflux temperature of the reaction mixture, over the reaction period.

Working up of the reaction product may be effected in conventional manner.

In one mode of effecting process variant b) of the invention, the compound of formula IV is produced in situ and the process is continued without isolation of the compound of formula IV.

The compounds of formula II, employed as starting material in the production of final compounds of formula I in accordance with process variant a), may be produced in known manner by condensing a compound of formula VI,

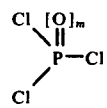  VI wherein $m$ is as defined above, with a compound of formula V in a molar ratio of at least $n:1$, $n$ being as defined above.

The process for the production of compounds of formula II may be effected as follows viz:

The compounds of formulae VI and V may be reacted in solution in a solvent such as a hydrocarbon solvent, e.g. benzene, toluene, xylene or cymene, or an ether solvent, e.g. diphenylether or a halogenated hydrocarbon, e.g. trichloroethylene or preferably in the absence of a solvent with excess of compound of formula VI. The reaction is preferably effected under anhydrous conditions and under an inert atmosphere, e.g. a nitrogen atmosphere. The reaction temperature may vary although the reaction is conveniently effected at the reflux temperature of the reaction mixture. At reflux temperature, the reaction is preferably effected in the absence of an acid binding agent, the hydrogen chloride formed during the reaction escaping from the reaction mixture. In such case, the reaction may be accelerated by a catalyst, e.g. potassium chloride. The reaction period will, of course, vary depending on the reaction conditions. Generally, however, a reaction period of between 5 and 50 hours, e.g. 7 to 48 hours, is sufficient.

After the reaction, the reaction product may be worked up in conventional manner.

As indicated above in relation to process variant a), the compound of formula II may be produced in situ and employed, without isolation, in the process for the production of the final compounds.

The compounds of formula IV, employed as starting material in the production of final compounds of formula I, in accordance with process variant b), may be produced by a process comprising condensing 1 mol of a compound of formula VI with 1 mol of a compound of formula III in manner known per se [Houben-Wehl, Methoden der Organischen Chemie, vol. XII / 2, P 277, 4th impression].

As indicated above in relation to process variant b), the compounds of formula IV may be produced in situ and, without isolation, employed directly in the production of final compounds of formula I.

The compounds of formula I possess flame retardant properties and are therefore useful as flame retarding agents. To this end, the compounds of formula I may be employed in a method of flame-proofing flammable organic materials, which comprises treating the organic material with a compound of formula I.

By the term "treating" is meant either surface coating or incorporation into the body of the organic material, in manner known per se.

By the term "flame-proofing," as used herein, is meant a reduction in, and not necessarily complete elimination of, the flammability of the organic material.

The above-mentioned method also forms a part of the present invention.

In one embodiment of the method of the invention, the compound is uniformly distributed throughout the organic material by mechanically mixing, e.g. kneading, the compound of formula I with either a particulate, e.g. granulated, form of the organic material or alternatively with a molten form of the organic material. This embodiment is particularly suited to polymer melts, e.g. polyolefins and polyesters.

In a further embodiment of the method of the invention, the compound is uniformly distributed throughout a flammable polymeric organic material by incorporation of the compound as the monomer or prepolymer stage of the production of the polymer, and the polymerisation process then effected. This further embodiment is particularly suited to certain polymeric organic materials such as polyurethanes.

After the flammable organic material has been treated in accordance with the method of the present invention, the organic material may, when appropriate, be formed into final shape, such as, by extrusion into, e.g. films, filaments or ribbons, or by moulding, e.g. injection moulding.

The compounds of formula I are, in general, heat stable and light stable to a significant degree and in addition are not prone to hydrogen halide release under normal conditions, in spite of their high halogen content.

The amount of the compound of formula I with which the organic material is treated in accordance with the method of the invention will, naturally, vary depending on the type of treatment, the compound employed, the nature of the organic material, the degree of flame proofing required and the required properties of the organic material so treated. However, in general, satisfactory results may be achieved when between 2 and 40%, preferably between 5 and 10%, of the compound is employed in relation to the weight of the organic material.

Examples of flammable organic materials to which the method of the invention is applicable are polyolefines, e.g. polyethylene and polypropylene, polyesters, polymethyl, methacrylates, polyphenylene oxides, polyurethanes, polystyrene, acrylonitrile-butadiene-styrene copolymers (ABS), polyamides, e.g. nylon, polypropylene oxide and polyacrylonitrile.

One example of the flame-proofing of a flammable organic material will now be described.

METHOD EXAMPLE

A compound of formula I is thoroughly mixed with polypropylene with polypropylene powder, in the ratio of 7:93 parts by weight respectively, the mixture is kneaded on a three-roll mill, and is then drawn off as a hide. The resulting hide is extruded into a sheet of 1 mm thickness.

The degree of flame-proofing may be established by determining the "limiting oxygen index" [Fenimore and Martin, Modern Plastics, Vol. 44 no 3, P 141 (1966)]. Essentially, the determination comprises supporting a specimen of the sheet vertically in a sealed chamber which is provided with an oxygen/nitrogen gas mixture inlet and also a burner for providing an open flame to which the specimen may be exposed. The oxygen content of the oxygen/nitrogen gas mixture is variable. The proportion of oxygen is varied and the amount at which no further propagation of burning of the sheet after exposure to the open flame is measured and yields the "limiting oxygen index." An index greater than the proportion of oxygen generally present in the atmosphere represents a flame proofing action.

Alternatively, the degree of flameproofing may be determined in accordance with German flammability test DIN 53,438. Essentially, this determination comprises supporting a specimen of the sheet vertically in a chamber and exposing the sheet to a naked flame under controlled conditions, for a period of 15 seconds. After removal of the flame, the period of further burning, and the length of burnt area is determined and compared with an untreated sheet.

A preferred class of compounds of formula I are the compounds of formula $I_{p_1}$

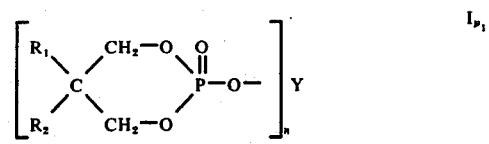

wherein $R_1$, $R_2$, $n$ and $Y$ are as defined above, namely, the compounds of formula $I_{p_1'}$

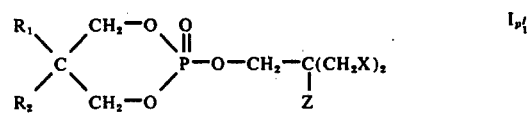

wherein $R_1$, $R_2$, $Z$ and $X$ are as defined above, the compounds of formula $I_{p_1''}$

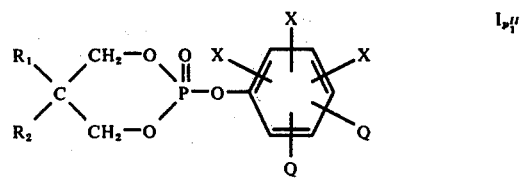

wherein $R_1$, $R_2$, $X$ and $Q$ are as defined above, the compounds of formula $I_{p_1'''}$

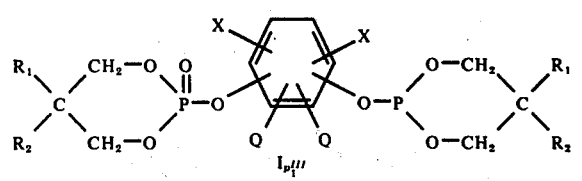

wherein $R_1$, $R_2$, $X$ and $Q$ are as defined above, and the compounds of formula $I_{p_1^{iv}}$

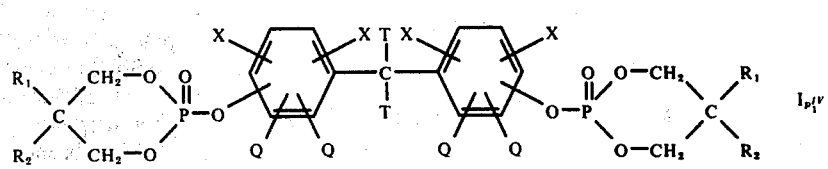

wherein $R_1$, $R_2$, X, and Q are T are as defined above.

A further preferred class of compounds of formula I are the compounds of formula $I_{p_2}$

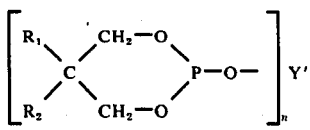 $I_{p_2}$ wherein $R_1$, $R_2$ and n are as defined above, and Y' is a radical $Y_1'$

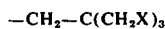 $Y_1'$ wherein X is as defined above, or a radical $Y_2'$

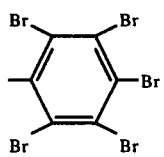 $Y_2'$ when n is 1, and y' is a radical $Y_3'$

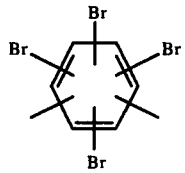 $Y_3'$ or a radical $Y_4'$

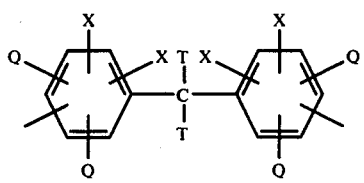 $Y_4'$ wherein X, Q and T are as defined above,
when n is 2, that is to say, the compounds of formula $I_{p_2'}$

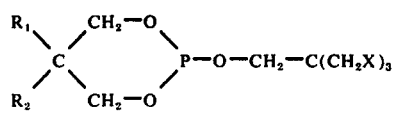 $I_{p_2'}$ wherein $R_1$, $R_2$ and X are as defined above, the compounds of formula $I_{p_2''}$

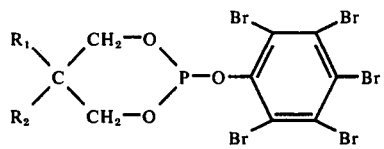 $I_{p_2''}$ wherein $R_1$ and $R_2$ are as defined above, the compounds of formula $I_{p_2'''}$

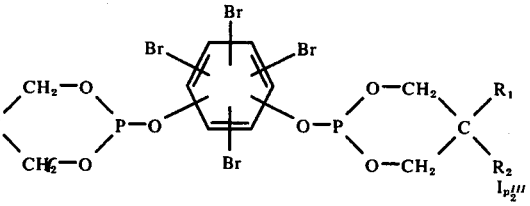 $I_{p_2'''}$ wherein $R_1$ and $R_2$ are as defined above, and the compounds of formula $I_{p_2^{IV}}$

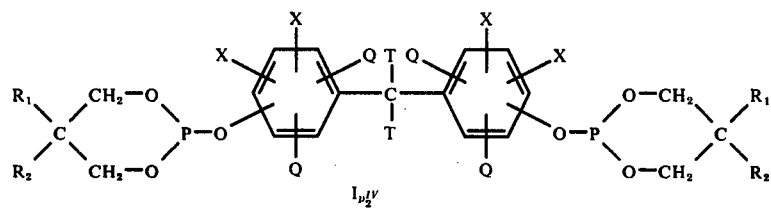

$I_{p_2^{IV}}$ wherein $R_1$, $R_2$ X, Q and T are as defined above.

Of particular interest are the compounds of formulae I, $I_{p_1}$, $I_{p_1'}$, $I_{p_1''}$, $I_{p_1'''}$, $I_{p_1^{IV}}$, $I_{p_2'}$, $I_{p_2''}$, $I_{p_2'''}$ and $I_{p_2^{IV}}$ wherein each $R_1$ and $R_2$ is, independently, hydrogen or alkyl of 1 to 3 carbon atoms.

Also of particular interest are the compounds of formulae I, $I_{p_1}$, $I_{p_1''}$, $I_{p_1'''}$, $I_{p_1^{IV}}$ and $I_{p_2^{IV}}$ wherein each Q is, independently, hydrogen, chlorine or bromine, especially hydrogen or bromine.

Also of particular interest are the compounds of formulae I, $I_{p_1}$, $I_{p_1^{IV}}$, $I_{p_2}$ and $I_{p_2^{IV}}$ wherein each T is, independently, hydrogen, methyl or ethyl.

Of special interest are the compounds of formulae I, $I_{p_1}$, $I_{p_1'}$, $I_{p_1''}$, $I_{p_1'''}$, $I_{p_1^{IV}}$, $I_{p_2}$, $I_{p_2'}$ and $I_{p_2^{IV}}$ wherein X is bromine.

Examples of the process of the invention will now be described. Where temperatures are referred to, these are in degrees Centigrade.

EXAMPLE 1: (process a) )

A mixture of 70 parts of 3-bromo-2,2-bis-(bromomethyl)-1-propanol, 2 parts of potassium chloride and 900 parts of phosphorus oxychloride is refluxed for 7 hours in a nitrogen atmosphere in the absence of moisture, the hydrogen chloride formed being allowed to escape. The potassium chloride is removed by filtration and the excess phosphorus oxychloride distilled. Then high vacuum is applied (0.2 Torr.) at 150° and 77 parts of phosphoric acid-[3-bromo-2,2-bis-(bromomethyl)-1-propylester]-dichloride is distilled over, which on cooling solidifies in crystalline form.

77 parts of the resulting crystals are stirred into 18.2 parts of neopentyl glycol and 175 parts of tetrahydrofuran, in the absence of moisture. Subsequently 33 parts of pyridine are added slowly at room temperature. The reaction solution is maintained at room temperature for 1 hour 30 minutes and thereafter for 38 hours at 50°, by which time the pyridine hydrochloride settles out. After cooling this is filtered off, the tetrahydrofuran distilled off and the residue suspended in water, on which a white solid is formed. The solid product is filtered off, washed with water and dried.

EXAMPLE 2: (process a))

A mixture of 258 parts of 2,4,6-tribromophenol, 4 parts of potassium chloride and 910 parts of phosphorus oxychloride is refluxed for 48 hours in a nitrogen atmosphere in the absence of moisture, the hydrogen chloride being allowed to escape. The potassium chloride is removed by filtration and the excess phosphorus oxychloride distilled off. Then in high vacuum (0.3 Torr.) and at 160°–162°, 285 parts of phosphoric acid-(2,4,6-tribromophenylester)-dichloride are distilled, which on cooling solidifies in crystalline form.

100 Parts of the resulting crystals are stirred into 23.2 parts of neopentyl glycol and 310 parts of tetrahydrofuran in the absence of moisture. Subsequently 38.4 parts of pyridine are slowly added, with external cooling to maintain the temperature at 20°. After 2 hours at 20° and then 24 hours at 50°, the tetrahydrofuran is distilled off; water is added to the residue, the resulting suspension filtered and the filter residue washed with water. The solid is dried and recrystallized from methanol.

EXAMPLE 3: (process b))

In the absence of moisture, 48.9 parts of pentabromophenol are mixed with 174 parts of toluene and 10.1 parts of triethylamine in a nitrogen atmosphere. A suspension of 18.45 parts of 2-chloro-2-oxo-5,5-dimethyl-1,3-2-dioxaphosphorinane [prepared as described in "Methoden der organischen Chemie" (Houben-Weyl), 4th impression, Vol. XII/2, p. 277] in 87 parts of toluene is added in small portions, whereupon a white precipitate is formed. The suspension is refluxed for 15 hours. After cooling, the solid is filtered off, washed with water, dried and recrystallized from chlorobenzene. It is obtained in the form of colourless crystals.

EXAMPLE 4: (process b))

63.9 Parts of tetrabromohydroquinone, 267 parts of tetrahydrofuran and 30.36 parts of triethylamine are mixed in a nitrogen atmosphere in the absence of moisture. A yellow solution is formed, to which is added slowly a solution of 55.35 parts of 2-chloro-2-oxo-5,5-dimethyl-1,3,2-dioxaphosphorinane (Example 3) in 133 parts of anhydrous tetrahydrofuran. An orange-coloured precipitate settles out. After 15 minutes the precipitate is filtered off, suspended in 700 parts of a 5% sodium hydrogen carbonate solution, filtered off and washed with water until neutral. The impurities are dissolved out in a 3:1 mixture of tetrahydrofuran-water. A colourless crystalline product is obtained.

EXAMPLE 5: (process a))

A solution of 65 parts of pentabromophenol, 1.5 parts of potassium chloride and 231.5 parts of phosphorus oxychloride is reacted for 48 hours at the refluxing temperature with stirring. After reaction the excess phosphorus oxychloride is distilled off at 20 mm Hg pressure. 81 Parts of a crystalline residue are obtained, which is dissolved in 300 parts of tetrahydrofuran. 17.8 Parts of 2-methyl-2-propyl-1,3-propanediol are added to the solution, followed in 15 minutes by 23.4 parts of pyridine. The mixture is held for a further 1 hour 30 minutes at room temperature, after which it is raised to 50° and reacted for 24 hours at this temperature. During the reaction the product settles out and after cooling to room temperature it is filtered off and washed with tetrahydrofuran. The solid product is then taken up with water with stirring and after further stirring for 10 minutes the suspension is filtered. The product can be recrystallized from chlorobenzene.

EXAMPLE 6: (process a))

A mixture of 70 parts of tetrabromo-o-cresol, 3.3 parts of potassium chloride and 250 parts of phosphorus oxychloride is reacted for 26 hours under reflux with stirring. On completion of the reaction the excess phosphorus oxychloride is distilled leaving 84 parts of a crystallizing oil. This is dissolved in 400 parts of tetrahydrofuran, with the subsequent addition of 16.2 parts of neopentyl glycol. After 25 minutes, 27 parts of pyridine are added at room temperature. After a further 30 minutes at room temperature the mixture is raised to 50° and reacted at this temperature for 24 hours. During the reaction a precipitate is formed, which after cooling to room temperature is filtered off and washed with tetrahydrofuran. It is then suspended in water, the suspension stirred further for 10 minutes and filtered. The resulting product can be recrystallized from chlorobenzene or dioxan.

The structure of the compounds of Examples 1 to 6 is identified in the Table below. Examples 7 to 10 of the Table are produced in analogous manner to the process of Example 1.

Table

| Example No. | m | Y | R₁ | R₂ | n | m.pt. |
|---|---|---|---|---|---|---|
| 1 | 1 | —CH₂—C(CH₂Br)₃ | CH₃ | CH₃ | 1 | 123–125° |
| 2 | 1 | 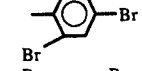 | CH₃ | CH₃ | 1 | 187–188° |
| 3 | 1 | 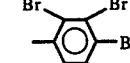 | CH₃ | CH₃ | 1 | 283–285° |
| 4 | 1 | 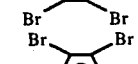 | CH₃ | CH₃ | 2 | 299–300° |
| 5 | 1 | 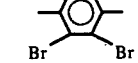 | CH₃ | C₃H₇ | 1 | 215° |
| 6 | 1 | 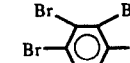 | CH₃ | CH₃ | 1 | 236° |
| 7 | 1 | 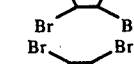 | H | H | 1 | 204° |
| 8 | 1 | 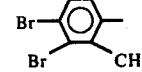 | H | H | 1 | 212° |

Table-continued

| Example No. | m | Y | $R_1$ | $R_2$ | n | m.pt. |
|---|---|---|---|---|---|---|
| 9 | 1 | 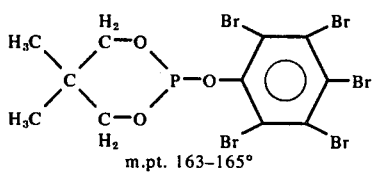 | $CH_3$ | $CH_3$ | 1 | 220° |
| 10 | 1 | 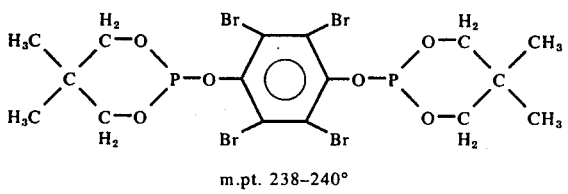 | $CH_3$ | $CH_3$ | 2 | 309–310° |

EXAMPLE 11: (process b) )

In the absence of moisture, 33.8 parts of 2-chloro-5,5-dimethyl-1,3,2-dioxaphosphorinane are diluted with 27 parts of tetrahydrofuran and added with stirring to a solution of 97.7 parts of pentabromophenol in 178 parts of tetrahydrofuran. Then at 5°–10°, 20.2 parts of triethylamine are gradually added over 30 minutes. The mixture is stirred further for 16 hours, the solid filtered off and washed with tetrahydrofuran. The filtrate is evapoated together with the wash solution. After recrystallization from acetic ethylester a white solid is obtained whose bromine and phosphorus content corresponds to the structural formula:

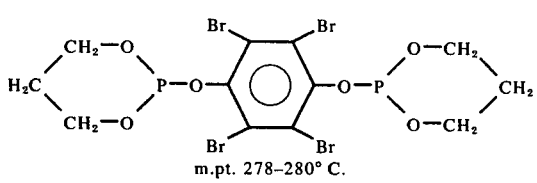

m.pt. 163–165°

EXAMPLE 12: (process b) )

In the absence of moisture, 47.3 parts of 2-chloro-5,5-dimethyl-1,3,2-dioxaphosphorinane and 59.5 parts of tetrabromohydroquinone are dissolved in 266 parts of tetrahydrofuran. In a nitrogen atmosphere, 28.3 parts of triethylamine diluted with 89 parts of tetrahydrofuran are added in 30 minutes at 15° with stirring. After a further 18 hours the white precipitate is filtered off and washed with benzene and tetrahydrofuran. The filtrate together with the wash liquid is evaporated. The remaining solid is recrystallized from acetic ethylester. Its bromine and phosphorus content corresponds to the structural formula

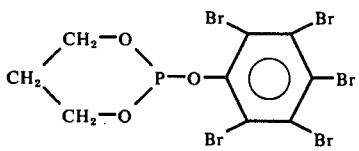

m.pt. 238–240°

EXAMPLE 13: (process b) )

A solution of 105.3 parts of a compound of the formula

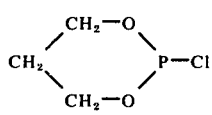

in 175 parts of tetrahydrofuran is added dropwise to a solution of 161.7 parts of tetrabromohydroquinone in 625 parts of tetrahydrofuran in 10 minutes at 10°–15° internal temperature in a nitrogen atmosphere. After this addition 76.9 parts of triethylamine diluted with 175 parts of tetrahydrofuran are added at the same temperature. Stirring is continued for 15 hours at room temperature. Subsequently the precipitated solid is filtered off and washed with tetrahydrofuran, the tetrahydrofuran removed and the remaining solid suspended in 260 parts of acetone and recrystallized from chlorobenzene. The white crystalline solid corresponds to the formula

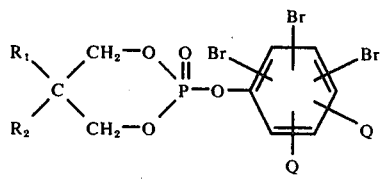

m.pt. 278–280° C.

The compound of formula

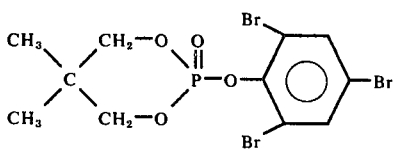

can be produced in an analogous manner. As the solubility of this compound is limited, the major proportion of the product settles out from the reaction mixture; it is filtered off with the triethylamine hydrochloride and separated from this by extraction with benzene. After removal of the benzene the product is recrystallized from tetrahydrofuran in the form of a white crystalline solid. m.pt. 181°–182° C.

What is claimed is:

1. A compound of the formula wherein $R_1$ and $R_2$ are each, independently, hydrogen or alkyl of 1 to 5 carbon atoms, and each Q is, independently, hydrogen, methyl, chlorine or bromine.

2. A compound of claim 1 wherein Q is hydrogen or bromine.

3. The compound of claim 2 of the formula

4. The compound of claim 2 of the formula

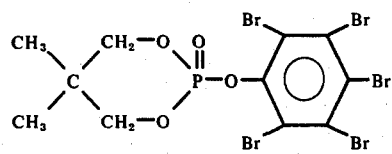
5. The compound of claim 2 of the formula
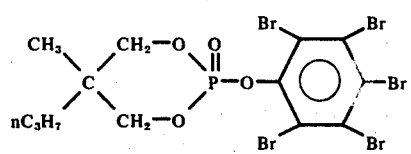
6. The compound of claim 1 of the formula
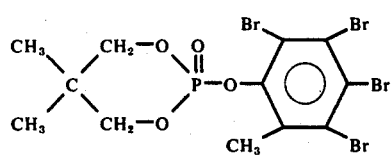
7. The compound of claim 2 of the formula
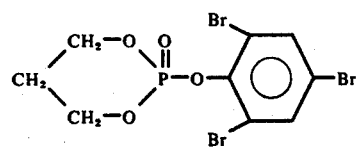
8. The compound of claim 2 of the formula
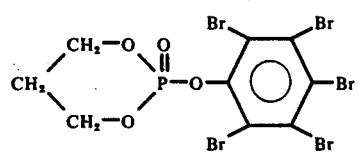
* * * * *